Figure 1:
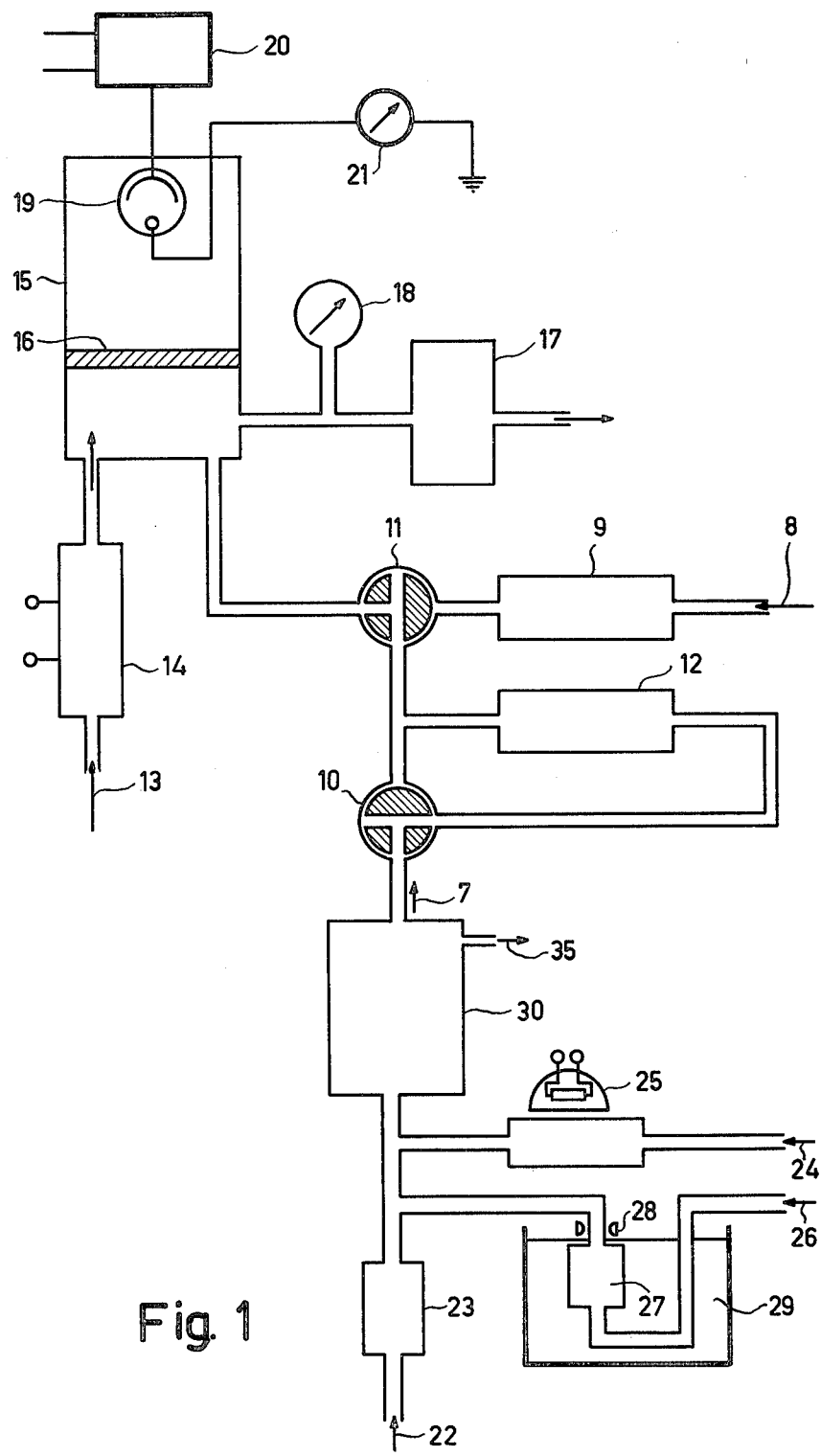

United States Patent [19]

Bullens et al.

[11] 4,221,761
[45] Sep. 9, 1980

[54] DEVICE FOR THE QUANTITATIVE REDUCTION OF NITROGEN DIOXIDE IN GAS MIXTURES

[75] Inventors: Valere G. J. Bullens; Hermanus Pauw; Rudy A. Falkenburg, all of Eindhoven, Netherlands

[73] Assignee: U.S. Philips Corporation, New York, N.Y.

[21] Appl. No.: 920,064

[22] Filed: Jun. 28, 1978

[30] Foreign Application Priority Data

Jul. 14, 1977 [NL] Netherlands ............... 7707839

[51] Int. Cl.² .................. G01N 31/00; C01B 21/24; C09K 3/00
[52] U.S. Cl. ................... 422/54; 423/405; 23/232 E; 23/927
[58] Field of Search .......... 422/52, 170, 171, 190, 422/191; 423/239, 405

[56] References Cited

U.S. PATENT DOCUMENTS

| | | | |
|---|---|---|---|
| 3,186,804 | 6/1965 | Fisher | 422/171 |
| 3,220,794 | 11/1965 | Stiles | 422/171 X |
| 3,382,033 | 5/1968 | Kitagawa | 423/239 |
| 3,476,524 | 11/1969 | Burke | 422/170 |
| 3,503,715 | 3/1970 | Haensel | 422/171 |
| 3,973,914 | 8/1976 | Van Heusden | 422/52 |
| 3,996,339 | 12/1976 | Falkenburg | 423/405 |

*Primary Examiner*—Michael S. Marcus
*Attorney, Agent, or Firm*—Norman N. Spain

[57] ABSTRACT

A reducer for the quantitative reduction of $NO_2$ to NO in gas mixtures. The reducer comprises two compartments of which one is filled with a granular preparation consisting of ferrosulphate and an acid alkalisulphate and the second comprises a granular preparation consisting of ferrosulphate and a strong acid. The preparation is preferably provided on the surface of granular inert carrier material, for example pumice.

1 Claim, 3 Drawing Figures

DEVICE FOR THE QUANTITATIVE REDUCTION OF NITROGEN DIOXIDE IN GAS MIXTURES

The invention relates to a device for the quantitative reduction of nitrogen dioxide to nitrogen monoxide. Such a device is of importance mainly in a device for the simultaneous determination of nitrogen dioxide and nitrogen monoxide in air while using the chemiluminescence reaction between NO and $O_3$.

This reaction is known per se, for example, from an article by A Fontijn, A. J. Sabadell and R. J. Ronco in J. Anal. Chem. 42, 575–579 (1970). The reaction energy is given off in the form of radiation in the wavelength range above approximately 600 nm. The intensity of said radiation is measured by a photomultiplier tube. In front of said photomultiplier there is a reaction vessel in which a mixture of NO and $NO_2$-containing air with a large excess of ozone gas is mixed. The ozone is obtained by means of a dark discharge from air or oxygen. The reaction is produced at a pressure of approximately 2 torr and follows the course according to the following equations:

$$NO + O_3 \rightarrow NO_2^* + O_2$$

$$NO_2^* \rightarrow NO_2 + h\nu.$$

Herewith the concentration of NO in the air sample is determined.

By passing the air sample through a reductor, the $NO_2$ present is converted quantitatively into NO. In an analysis of the thus reduced air sample, the sum of $NO + NO_2$ in the orignial sample is determined as NO. The concentration of $NO_2$ having originally been present can now be calculated.

U.S. Pat. No. 3,996,339 discloses such a device for the quantitative reduction of $NO_2$ to NO in gas mixtures. Said device comprises a container having an inlet and an outlet and filled with a granular preparation consisting of a mixture of ferrous sulphate and an acid alkali sulphate in a molecular ratio between 3:1 and 1:1. The preparation is preferably provided on the surface of an inert carrier, for example pumice.

It has now been found, however, that, in particular with a low moisture content of the gas sample and in the presence of ozone, an interfering side reaction occurs, namely the reaction $$2NO_2 + O_3 \rightleftharpoons N_2O_5 + O_2$$

in which the $N_2O_5$ formed decomposes only very slowly, cannot be reduced to NO by the reducer and hence gives rise to incorrect analysis results in as far as the second part of the analysis, after reduction, is concerned.

It is an object of the invention to provide an improvement of the device in that sense that the result of the interfering side reaction is eliminated and correct analysis results are obtained.

The device according to the invention is characterized in that a gas-permeable partition is present in the container so that a second compartment is present beside the first, said second compartment comprising a granular preparation consisting of a mixture of ferrous sulphate and a strong acid of a pK-valve in aqueous solution of at most 4 in a molecular ratio between 1:1 and 1:5, the overall weight ratio of active components in the first compartment with respect to the second compartment exceeding 1:2. The last-mentioned weight ratio is preferably larger than 1:1.

The operation of the thus improved device is such that ozone present in the sample gas is converted in the first compartment into oxygen and that a part of the $NO_2$ (approximately 10% by volume) is reduced to NO. The remaining $NO_2$ is reduced quantitatively to NO in the second compartment containing acid alkali sulphate.

The acid of pK value in aqueous solution of at most 4 may be tartaric acid (pK = 2.98), citric acid (pK = 3.14), sulphuric acid (PK = 1.92 in 0.01 n solution) or oxalic acid (pK = 1.23).

As in the above-mentioned U.S. patent specification, the granular preparation in the device according to the invention may also be provided on grains of an inert carrier material, preferably having a large surface area. For this purpose, the carrier material is wetted in a vacuum with a concentrated solution of the said salts and/or acids and the grains are then dried in a vacuum. A 1 molar solution of ferrous sulphate + potassium bisulphate has a pH of approximately 5; a 1 molar solution of ferrous sulphate + tartaric acid has a pH of approximately 2. The inert carrier material is, for example, pumice, silica, quartz or polytetrafluoroethylene.

The partition between the two compartments may be inter alia a plug of glass wool, a plate of porous sintered glass powder or porous sintered Alundum.

In a device for determining the $NO_x$-content of polluted air by means of chemiluminescence a comparison is now made, by way of example, between the device according to the invention and a known device according to U.S. Pat. No. 3,996,339.

The invention will now be described in greater detail with reference to FIG. 1 which is a diagrammatic view of an apparatus according to the invention for the simultaneous determination of nitrogen dioxide and nitrogen monoxide in air by the chemiluminescence reaction between NO and $O_3$.

The part of the drawing in FIG. 1 above the element 30 shows a device for the simultaneous determination of NO and $NO_2$ in air. In the drawing, 7 denotes the inlet for the air to be analysed and 8 is an inlet for air which supplies nitrogen oxide-free air via the filter 9 so as to determine the zero point of the device. The device has three-way valves 10 and 11 which, in the position as shown in FIG. 1, enable the determination of the sum of $NO + NO_2$ calculated as NO.

Figure 2:
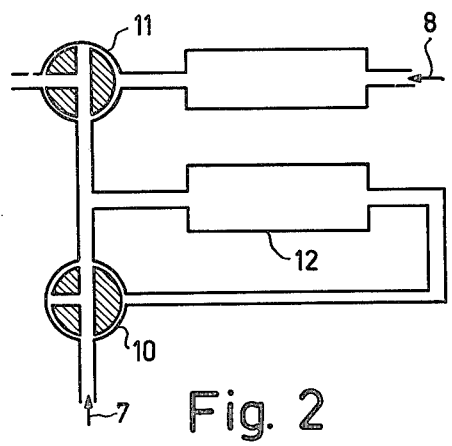

FIG. 2 shows a part of the device in which the three-way valves 10 and 11 have such a position that the content of NO is determined. The position of the valves in which the zero point is determined will be obvious. The device for the quantitative reduction of nitrogen dioxide to nitrogen monoxide is denoted by 12.

Figure 3:
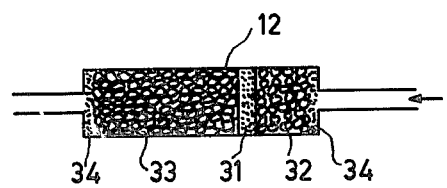

FIG. 3 shows the device according to the invention in detail. The filling 32 in the right-hand compartment is obtained from pumice having a grain size of 6–7 mesh (approximately 2.8–3.4 mm). and a specific surface area of 100–200 m²/g, which is impregnated with a mixture of $FeSO_4.7H_2O$ and tartaric acid in a molecular ratio of 1:3 by wetting the grains with a concentrated solution and then evaporating them to dryness. The filling 33 in the left-hand compartment consists of pumice of the same qualification which is impregnated with a mixture of $FeSO_4.7H_2O$ and $KHSO_4$ in a molecular ratio 1:1. A plug of glass wool 31 is present between the two compartments. At the ends 34 a plug of glass wool is present. The length of the reductor 12 is 15 cm, that of the compartment 33 is 11 cm and that of the compartment 32 is 3 cm. The inside diameter is 2 cm.

The determination of NO takes place by photometric measurement of the emitted chemiluminescence radiation which occurs by reaction of NO with ozone in the space 15. The reaction light impinges, via the optical filter 16 which absorbs radiation below 600 nm, on the photomultiplier tube which is fed by the high-voltage unit 20. The photoflux which is measured by the ammeter 21 is a measure of the NO concentration. The ozone is supplied by the ozonizer 14 which draws in pure air or oxygen 13 and in which a dark discharge is maintained with an alternating voltage of approximately 6 kV.

The gas is sucked off by the pump 17 controlled by manometer 18.

The part of FIG. 1 below reference numeral 7 denotes the apparatus with which the dosing of components to a gas flow is possible for the comparison of the reductor according to the invention with that according to the Specification mentioned above.

Dry pure air is supplied at 22. By means of humidifier 23 a doses moisture content can be added to said air. Nitrogen is supplied through inlet 26. A dosed quantity of $NO_2$ is supplied by means of $NO_2$ source 27 which is present within a thermostat 29 and a flow limiter 28. Oxygen is supplied through 24. A fraction hereof is converted into ozone by the u.v.-supplying discharge source 25; the concentration can be adjusted by means of the intensity of the current through the u.v. 1map. In compartment 30 the components are mixed and are then supplied to the $NO$-$NO_2$ monitor described above. The excess of said gas flows away via outflow aperture 35. The valves have the position of FIG. 1.

With a dosed $NO_2$ concentration of 60 parts per $10^9$ the recording ammeter gives a deflection of 45.5 scale units. The reduction unit 12 is that according to the invention, shown in FIG. 3. When 100 parts per $10^9$ of ozone are dosed to the gas flow, the scale deflection does not vary, nor does it vary when the ozone dosing is discontinued.

In an experiment in which 12 is the device according to U.S. Pat. No. 3,996,339, that is to say comprising only one compartment which is filled only with pumice covered superficially with $FeSO_4.7H_2O$ and $KHSO_4$, $NO_2$ is dosed in a quantity of 70 parts per $10^9$, which gives a scale deflection of 62.5. When 90 parts per $10^9$ of ozone are added, the deflection drops to 60.0. When the supply of ozone is discontinued, a deflection is found of 64.0 which gradually returns to 62.5. The relative humidity in these experiments was 10–15%. At higher relative humidities the interference is proportionally smaller.

What is claimed is:

1. In an apparatus for simultaneously determining the amounts of nitrogen monoxide and nitrogen dioxide in air by means of an apparatus comprising an ozonizer suitable for supplying a continuous stream of ozone, a reaction chamber positioned to receive ozone from said ozonizer and air containing nitrogen oxide or air free of nitrogen oxide and containing a photomultiplier for measuring the luminescence emmission of the reaction between nitrogen monoxide and ozone, a conduit connecting said ozonizer to said reaction chamber for transferring said ozone to said reaction chamber, a gas conduit opening into said reaction chamber containing a valve suitable for admitting air free of nitrogen oxide or air to be analyzed through said conduit opening into said reaction chamber, a reducer connected to said valve for reducing nitrogen dioxide in the air to be analyzed to nitrogen monoxide and a valve by-passing conduit for by-passing the reducer, the improvement wherein said reducer comprises a container having an inlet and an outlet and divided into two compartments separated from each other by a gas-permeable partition, one of said compartments is filled with a granular mixture of ferrous sulphate and an alkali metal acid sulphate in a molar ratio of from 3:1 to 1:1, the other of said compartment is filled with a granular mixture of ferrous sulphate and a strong acid, the pK value of which in aqueous solution is at most 4, in a molecular ratio between 1:1 and 1:5 and wherein the overall weight ratio of the ferrous sulphate containing mixture in the first compartment with respect to the ferrous sulphate containing mixture in the second compartment exceeds 1:2, said mixtures being respectively supported by inert granular carrier material.

* * * * *